United States Patent [19]

De Vincentiis

[11] Patent Number: 4,501,914

[45] Date of Patent: Feb. 26, 1985

[54] 2-HYDROXY-3-(O-METHOXY-PHENOXY)-PROPYL 2-(P-ISOBUTYL-PHENYL)-PROPIONATE AND PHARMACEUTICAL COMPOSITIONS CONTAINING THE SAME

[75] Inventor: Leonardo De Vincentiis, Rome, Italy

[73] Assignee: Ausonia Farmaceutici S.r.l., Pomezia, Italy

[21] Appl. No.: 441,106

[22] Filed: Nov. 12, 1982

[30] Foreign Application Priority Data

Mar. 10, 1982 [IT] Italy ............................. 20073 A/82

[51] Int. Cl.³ ............................................ C07C 69/76
[52] U.S. Cl. ..................................... 560/105; 514/544
[58] Field of Search .......................................... 560/105

[56] References Cited

U.S. PATENT DOCUMENTS 4,134,989  1/1979  Baiocchi et al. .................... 560/105
4,150,137  4/1979  Noda et al. ......................... 560/105

Primary Examiner—Paul J. Killos
Attorney, Agent, or Firm—Walter H. Schneider

[57] ABSTRACT

2-Hydroxy-3-(o-methoxy-phenoxy)propyl 2-(p-isobutyl-phenyl)-propionate of formula (I)

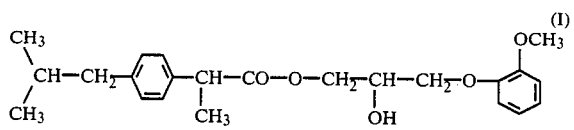

has marked analgesic, anti-inflammatory and mucoregulatory properties.

2 Claims, No Drawings

2-HYDROXY-3-(O-METHOXY-PHENOXY)PROPYL 2-(P-ISOBUTYL-PHENYL)-PROPIONATE AND PHARMACEUTICAL COMPOSITIONS CONTAINING THE SAME

The present invention relates to 2-hydroxy-3-(o-methoxyphenoxy)propyl 2-(p-isobutyl-phenyl)-propionate of formula (I)

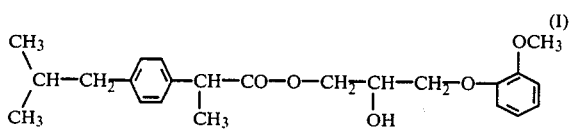

The anti-inflammatory activity of 2-(p-isobutylphenyl)-propionic acid or Ibuprofen is known. In this respect reference should be made, for example, to Adams et al., Arch Pharmacodyn. Ther 178, 115 (1969). Although the abovementioned drug has good therapeutic properties it has the drawback of causing considerable gastric lesions.

It is also known to use 3-(o-methoxyphenoxy)-1,2-propandiol(guaiaphenesine) as an expectorant (see for example Merck Index, 9th Ed., 4402).

It has been discovered that whilst 2-hydroxy-3-(o-methoxyphenoxy)propyl 2-(p-isobutyl-phenyl)-propionate acts as a bronchosecretogogue and mucosecretolyte in a manner comparable to guaiaphenesine in equal doses by weight, it has analgesic and antipyretic effects which are in practice the same as those of Ibuprofen with respect to which it has the considerable advantages of an anti-inflammatory activity which is greater in certain tests and in any case of longer duration, and a comparatively low degree of gastric lesion.

In addition the compound (I) has a pharmacokinetic profile which is favourable both with respect to that of Ibuprofen and guaiaphenesine, and a marked pulmonary tropism.

The invention also relates to pharmaceutical compositions containing 2-hydroxy-3-(o-methoxy-phenoxy)-propyl 2-(p-isobutyl-phenyl)-propionate as the active principle.

The invention relates lastly to a method for the preparation of the 2-hydroxy-3-(o-methoxy-phenoxy)propyl 2-(p-isobutylphenyl)-propionate, characterised in that 2-(p-isobutyl-phenyl)-propionic acid chloride (II) is reacted with 3-(o-methoxyphenoxy)-propandiol (III) in accordance with the following equation:

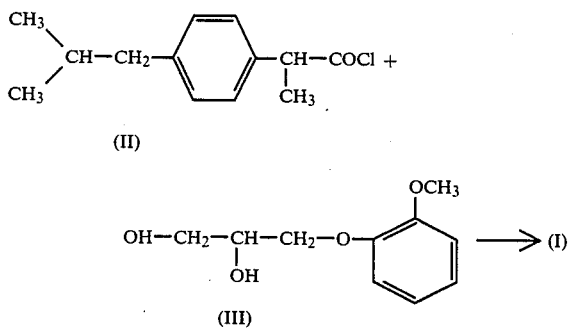

The reaction is preferably carried out in aprotic solvents, such as dichloromethane, tetrahydrofurane, diethyl ether, and in the presence of acidity acceptors, preferably pyridine or triethylamine.

The reaction temperatures are within the range of approximately 0° C. to approximately 60° C. The reaction is preferably carried out at ambient temperature.

The following example illustrates the method of the invention without, however, limiting it in any way.

EXAMPLE 5 g (0.0229 mole) of 2-(p-isobutylphenyl)propionic acid chloride dissolved in 50 ml of dichloroethane were added with mechanical stirring and at ambient temperature to a solution of 20 ml of dichloromethane containing 3 ml of pyridine and 4.7 g of 3-(o-methoxy-phenoxy)-propandiol. The mixture was left in these conditions for 2 hours. At the end of this time the mixture was washed with dilute HCl and the two phases were separated. The organic phase was dried on anhydrous sodium sulphate and evaporated at reduced pressure in order to remove the solvent.

The raw material obtained in this way was subjected to chromatography on $SiO_2$, with preliminary elution with petroleum ether and then petroleum ether/diethyl ether 1:1.

In this way 6.7 g of a dense oil which could not be crystallized, was soluble in common organic solvents, and non-dispersed in TLC was obtained. The structure of the product was confirmed by the analytical and spectroscopic data.

Elemental Analysis for $C_{23}H_{30}O_5$ theory (%): C=71.48; H=7.82 yield (%): C=71.52; H=7.88

IR Spectrum recorded in liquid film (the values of the absorption bands are expressed in $cm^{-1}$):

Stretch O—H 3600–3200 broad band Stretch C=O 1735 Stretch C=C 1585 Stretch C—O 1250

$H^1$ NMR Spectrum recorded in deuterochloroform using TMS as the reference (the values of the chemical displacements of the protons are expressed as δ):

0.9 (d, 6H, HC(CH_3)_2); 1.5 (d, 3H, CH—CH_3); 1.9 (m, 1H, CH_2—CH(CH_3)_2); 2.45 (d, 2H, CH_2—CH(CH_3)_2; 2.7–3.3 (m, 1H, OH variable); 3.6–4.3 (m, 9H, OCH_3—CH—COO—,

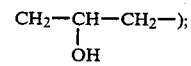

6.8–7.3 (m, 8H aromatics)

The biological and pharmacological characteristics of the product—which is called hereafter, for the sake of brevity, AF 860 are described as follows.

Toxicity

The acute toxicity was tested on various species of animal using Litchfield and Wilcoxon's Method (J. Pharm. Exp. Therap., 96, 99–113 (1949).

The results are shown in Table 1.

TABLE 1

|   | Specie | Admin. | $LD_{50}$ |
|---|--------|--------|-----------|
| AFP 860 | Mouse | per os | 1850 |
| AFP 860 | Rat | per os | 2510 |
| AFP 860 | Rabbit | per os | 3300 |

Anti-inflammatory activity Carrageenin oedema

The tests were carried out on rats, using a test in which a subplantar oedema was induced by carrageenin.

AFP 860 and, for comparison, 2-(p-isobutylphenyl)-propionic acid (Ibuprofen) were administered orally 30 minutes before the carrageenin at the dosages specified below.

When the oedema had been induced, the animals in each group were monitored, every 60 minutes for 5 consecutive hours in order to ascertain the development of the inflammatory process.

The results obtained, expressed as oedematous paw volumes, are given in Table 2. From the comparison between the control rats and those treated with AFP 860, it is obvious that the latter has an excellent anti-inflammatory activity which is comparable to that of Ibuprofen in the experimental conditions and dosages used.

TABLE 2

| | | MEAN PAW VOLUME | | | | | | AREA | % |
|---|---|---|---|---|---|---|---|---|---|
| | DOSAGE | AT VARIOUS TIMES | | | | | | | |
| | mg/kg | DURING TREATMENT | | | | | | Absolute | % inhibition |
| TREATMENT | per os | 0 | 1 | 2 | 3 | 4 | 5 | value | over controls |
| Controls | — | 22.5 | 29.8 | 36.2 | 39.9 | 43.3 | 43.9 | 310.6 | — |
| Ibuprofen | 100 | 21.9 | 27.8 | 29.3 | 31.4 | 32.7 | 35.3 | 184.0 | 40.8 |
| AFP 860 | 150 | 22.1 | 27.1 | 30.2 | 31.6 | 32.2 | 34.7 | 176.5 | 43.2 |

TABLE 3

| | | Pleurisy induced by carrageenin | | | | | |
|---|---|---|---|---|---|---|---|
| TREATMENT | DOSAGE mg/kg per os | No. ANIMALS | HOURS | VOLUME | % inhib. over control | % leukocytes × 1000 | % inhib. over control |
| Controls | | 10 | 5 | 0.95 | = | 17,540 | = |
| | | | 24 | 0.83 | = | 18,320 | = |
| AFP 860 | 100 | 10 | 5 | 0.54 | 43.18 | 5,130 | 70.75 |
| | | | 24 | 0.43 | 48.19 | 7,190 | 60.75 |
| Ibuprofen | 100 | 10 | 5 | 0.52 | 45.26 | 5,380 | 69.32 |
| | | | 24 | 0.72 | 13.25 | 16,950 | 7.47 |

Pleurisy induced by carrageenin

The method described by Vinegar et al. (Vinegar R., Irvaux J. F., Selph J. I., Proc.Soc.Exp.Biol.Med., 143, 3 (1973) was used.

Sprague-Dawley rats of both sexes weighing between 150 and 200 g were used. The animals were divided into "at random" groups and were starved on the previous day with water ad lib.

The compounds in question were administered orally 30 minutes before the intrapleural injection at an equal dose by weight of 100 mg/kg. The results are shown in Table 3.

Comparison of the results shows that AFP 860 causes a 43.18% reduction of the exudate resulting from the carrageenin induced pleurisy at the fifth hour after the treatment of the animals and a 70.75% reduction of the number of leukocytes present at the same time (reductions of the same order of magnitude as those produced by the comparison drug, at equal doses by weight, i.e. 45.26% for the exudate and 69.32% for the number of leukocytes).

After 24 hours, AFP 860 was exerting a protective action which was much greater than that of Ibuprofen. AFP 860 produced a 48.19% reduction of the volume of the exudate and a 60.75% reduction of the number of leukocytes, whilst the comparison drug only reduced the volume of the exudate by 13.25% and the number of leukocytes by 7.47%.

On the basis of this research, and bearing in mind that the two drugs were used in equal doses by weight and not equal doses by molecule and also bearing in mind the number of leukocytes present and the volume of the pleural exudate, it can be seen that there was an anti-inflammatory activity which was greater in absolute terms and of longer duration using the AFP 860 with respect to the comparison drug.

This increased pharmacological activity is probably due to a pulmonary tropism on the part of AFP 860 which was surprisingly ascertained during pharmacokinetic research.

Muscle relaxant activity

Use was made of the method of Kondziella (1964) which consists in suspending the mice from a metal grille and in recording the number of animals which remain suspended for more than 30 seconds. The animals which fall off during this time period are considered to be subject to muscle relaxation.

A metal grille having a 7 mm mesh and a surface area of 2×2 m disposed horizontally at 1.5 m from the ground was used for this test. The mice were selected on the day preceding the test, rejecting those which fell within 30 seconds. These were then divided into 7 at random groups and starved. AFP 860 and, for comparison purposes, mephenesine both suspended in 1% carboxymethylcellulose were administered per os at dosages of 150 mg/kg in the case of AFP 860 and 100 mg/kg in the case of mephenesine. A third group of mice acting as the control received 1% CMC in equal volumes to those used for the mice treated with the drugs.

For each mouse the grille suspension tests were carried out 15 and 30 minutes after administration of the drugs in order to enable the evaluation of the time of maximum activity and then every 30 minutes until the muscle relaxant effect had completely disappeared in order to establish the duration of this effect.

The parameter used for evaluating the results was the percentage of animals subject to muscle relaxation with respect to those treated. As can be seen from Table 4, both AFP 860 and mephenesine produced, at the dosages tested, a considerable muscle relaxant effect of the same size, i.e. 60% of animals subject to muscle relaxation with respect to the controls, in the mice.

TABLE 4

Muscle relaxant effect of AFP 860 and mephenesine on the mouse (metal grille test)

| No. Animals | Drug | mg/kg/os | % animals subject to muscle relaxation |
|---|---|---|---|
| 10 | GMC 1% | — | 0 |
| 10 | AFP 860 | 150 | 60 |
| 10 | Mephenesine | 100 | 60 |

Analgesic activity

Use was made of the test involving contortions induced by phenylquinone in the mouse based on the method described by Siegmund et al. (Proc.Soc.Exp.Biol.Med., 95, 729 (1957). AFP 860 was administered orally at a dosage of 100 mg/kg in comparison with Ibuprofen at the same dosage. The two drugs were administered 30 minutes before the intraperitoneal injection of phenylquinone. The excellent analgesic activity of AFP 860, slightly inferior to that of Ibuprofen administered at an equal dosage by weight, is shown by the results obtained and given in Table 5.

TABLE 5

Analgesic activity - Phenylquinone contortions in the mouse

| Treatment | Dose mg/kg os | Mean No. of Contortions | % inhib. over controls | No. animals undergoing contortions |
|---|---|---|---|---|
| Controls | — | 13.2 ± 2.8 | — | 10/10 |
| Ibuprofen | 100 | 1.8 ± 0.6 | 82.26 | 1/10 |
| AFP 860 | 100 | 3.9 ± 1.4 | 70.45 | 2/10 |

Antipyretic activity

The test was carried out using male rats on the basis of the method described by Boisser et al. (Boisser J. R., Simon P., Therapie 17, 1225 (1962). Using this method hyperthermia was produced by means of the subcutaneous administration of yeast.

When the hyperthermia was evident, the rats were treated orally with AFP 860 and, for comparison, with Ibuprofen at the dosages described below.

The temperature variations, taken every hour for five successive hours after the treatment are given in Table 6. In these experimental conditions, AFP 860 shows a very good antipyretic activity, which is in practice the same as that of Ibuprofen, used for comparison.

TABLE 6

Antipyretic activity - Hyperthermia induced by yeast

| Treatment | Dose mg/kg p.o. | Weight g. | Rectal Temperature °C. basic | 1 h | 2 h | 3 h | 4 h | 5 h | % inhib. over controls |
|---|---|---|---|---|---|---|---|---|---|
| Controls - Hyperthermic animals | — | 183.5 | 38.4 | 38.3 | 38.2 | 38.0 | 38.4 | 37.9 | — |
| Blank Controls | — | 168.7 | 37.2 | 37.2 | 37.6 | 37.7 | 37.6 | 37.7 | — |
| Ibuprofen | 100 | 184.5 | 38.8 | 38.0 | 37.7 | 37.3 | 37.5 | 37.4 | 119.0 |
| AFP 860 | 150 | 186.0 | 38.4 | 37.7 | 37.7 | 37.5 | 37.3 | 37.2 | 127.0 |

Gastrolesive action

Rats starved for 18 hours were treated orally with AFP 860 and, for comparison, with Ibuprofen, at the dosages given below. 5 hours and 30 minutes after the treatment the animals were killed and removal of the stomach was carried out in order to enable examination of the gastric mucosa.

As can be seen from the results obtained and given in Table 7, the gastrolesivity of AFP 860, in the experimental conditions used, was much lower than the Ibuprofen used for comparison.

TABLE 7

| | Gastrolesive action | |
|---|---|---|
| Treatment | Dose mg/kg/os | Mean dimensions (mm) Ulcers |
| Controls | — | 0 |
| Ibuprofen | 100 | 8.7 ± 1.4 |
| AFP 860 | 150 | 0.8 ± 0.3 |

Bronchosecretogogue activity

Bronchosecretogogue activity was determined in Wistar rats by means of per os administration using the method of Mawatari (Mawatari H., Kagoshima Daiagaku Igaku-Zasshi, 27, 561 (1976), and comparing AFP 860 and guaiaphenesine at the dosages given below. The results are shown in Table 8.

TABLE 8

Bronchosecretogogue activity (Mawatari's technique)

| Compound | Adm. Dosage mg/kg/os | No. animals | % increase of FlNa* with respect to controls |
|---|---|---|---|
| AFP 860 | 500 | 10 | 24.5 |
| Guaiaphenesine | 500 | 10 | 20.3 |

*Sodium fluorescein

Examination of the values given shows that AFP 860 exerts a considerable effect as a bronchosecretogogue which may in practice be considered superimposable to that of guaiaphenesine used in equal doses by weight in the experimental conditions used.

Mucosecretolytic activity

Mucosecretolytic action was tested on male rabbits using the technique of Giraldez, Grass and Bruseghini (Abstr.Comp.Int.Pharm. N. 1086—Paris 1978) by means of oral administration and comparing AFP 860 with guaiaphenesine at the dosages given below. The results are given in Table 9.

TABLE 9

Mucosecretolytic activity (technique of Giraldez et al.)

| Compound | Dose mg/kg/os | No. animals | % increase of bronchial secretion over controls |
|---|---|---|---|
| AFP 860 | 500 | 10 | 32.7 |
| Guaiaphenesine | 500 | 10 | 34.4 |

The values obtained in the test show that AFP 860 has remarkable secretolytic activity which is comparable with that of guaiaphenesine used as a comparison at the same dosages by weight.

Pharmacokinetics

AFP 860 was administered at a dosage of 50 mg/kg per os to Charles River albino rats having a weight of approximately 200 g. A second batch of rats were administered per os with Ibuprofen at a dosage of 27 mg/kg, i.e. equimolar with respect to AFP 860. A third batch of rats were administered per os with guaiaphenesine at a dosage of 27 mg/kg, i.e. equimolar both with respect to AFP 860 and Ibuprofen.

The animals were killed in groups of 3 after 15 minutes, 30 minutes, 1 hour, 2 hours, 4 hours and 6 hours. Ibuprofen and guaiaphenesine were extracted and determined by means of high pressure liquid chromatography using an UV detector at a wavelength of 275 nm. Ibuprofen was determined in the lungs of the rats killed after 30 minutes and 1 hour. The plasma levels of Ibuprofen observed after the administration of AFP 860 had a greater degree of latency with respect to the administration of Ibuprofen per se. The Ibuprofen peak on average appeared 30 minutes (24 μg/ml) after the administration of Ibuprofen and 1 hour (22.8 μg/ml) after the administration of AFP 860. At the end of the first hour the Ibuprofen levels were higher after the administration of AFP 860 than after the administration of Ibuprofen per se, and remained as such up to the sixth hour.

The area under the plasma level curve (AUC) for Ibuprofen was 63.4 $\mu g.ml^{-1}.h$ after the administration of AFP 860 and 49.0 $\mu g.ml^{-1}.h$ after the administration of Ibuprofen per se. In practice, AFP 860 provides a greater degree of latency and an improved bio-availability both with respect to Ibuprofen and guaiaphenesine.

Pulmonary tropism

As the pulmonary concentrations of Ibuprofen both in rats treated with AFP 860 and rats treated with Ibuprofen were available, it was possible to ascertain the Ibuprofen concentration ratio between the lung and the plasma. The ratios were as follows:

|  | Ibuprofen concentration ratio between lung and plasma | |
|---|---|---|
|  | 30 mins | 1 hour |
| AFP 860 | 0.5 | 0.7 |
| Ibuprofen | 0.2 | 0.3 |

The values given show that AFP 860 has a marked pulmonary tropism.

The compound of the invention has therefore been shown to have a high degree of analgesic, antipyretic and anti-inflammatory activity, together with substantial effects as a bronchosecretogogue and a mucusecretolyte.

On the basis of the above comments it can be seen that the compound AFP 860 is suitable for use as an elective drug in the treatment of muscular inflammation and diffuse pain following diseases of the influenza type and as a symptomatolytic in cold infections associated with acute or chronic catarrhal conditions.

The present invention also relates to all the aspects of industrial use related to the use of AFP 860 as an analgesic anti-inflammatory, antipyretic and muco-regulatory agent. For this reason an essential aspect of the invention is constituted by pharmaceutical formulations containing predetermined amounts of AFP 860, together with vehicles, excipients, preserving agents etc. commonly used in pharmaceutical techniques. The compound of the invention may for example be administered orally in the form of capsules, suspensions, single dose sachets containing granules, or rectally in the form of suppositories.

I claim:

1. 2-hydroxy-3-(o-methoxy-phenoxy)propyl 2-(p-isobutylphenyl)-propionate of formula (I)

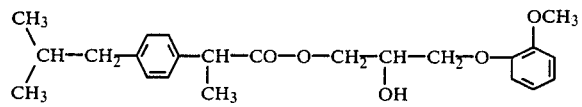

as a new compound.

2. Pharmaceutical compositions having analgesic, anti-inflammatory, antipyretic, bronchial secretion increasing and muco-secretolytic activity, characterised in that they contain the compound as claimed in claim 1 as the active principle.

* * * * *